(12) United States Patent
Felenc

(10) Patent No.: US 11,819,297 B2
(45) Date of Patent: Nov. 21, 2023

(54) LIGHT GUIDED DIGITIZATION METHOD TO REGISTER A BONE

(71) Applicant: Think Surgical Inc., Fremont, CA (US)

(72) Inventor: Eustache Felenc, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 787 days.

(21) Appl. No.: 16/722,007

(22) Filed: Dec. 20, 2019

(65) Prior Publication Data
US 2020/0197113 A1 Jun. 25, 2020

Related U.S. Application Data

(60) Provisional application No. 62/782,951, filed on Dec. 20, 2018.

(51) Int. Cl.
| | |
|---|---|
| *A61B 34/30* | (2016.01) |
| *A61B 90/00* | (2016.01) |
| *A61B 34/20* | (2016.01) |
| *A61B 34/10* | (2016.01) |

(52) U.S. Cl.
CPC .............. *A61B 34/30* (2016.02); *A61B 34/10* (2016.02); *A61B 34/20* (2016.02); *A61B 90/39* (2016.02); *A61B 2034/102* (2016.02); *A61B 2034/105* (2016.02); *A61B 2034/2055* (2016.02); *A61B 2034/2068* (2016.02); *A61B 2034/304* (2016.02); *A61B 2090/3916* (2016.02); *A61B 2090/3945* (2016.02)

(58) Field of Classification Search
CPC .................... A61B 34/20; A61B 2034/2055
See application file for complete search history.

(56) References Cited

U.S. PATENT DOCUMENTS

| | | | | |
|---|---|---|---|---|
| 5,792,147 A | * | 8/1998 | Evans ............. | G16H 40/63 |
| | | | | 606/130 |
| 2009/0068620 A1 | * | 3/2009 | Knobel ............. | A61B 34/20 |
| | | | | 433/223 |
| 2018/0235715 A1 | * | 8/2018 | Amiot ............. | G01B 11/25 |

* cited by examiner

*Primary Examiner* — Andrew Yang
(74) *Attorney, Agent, or Firm* — MaxGoLaw PLLC

(57) ABSTRACT

A system, device, and method is provided that improves the point collection process during bone registration for computer-assisted surgical procedures. A user is guided in the point collection process by projecting a set of points directly on the bone with a tracked digitizer probe following a rough registration of the bone. The system, device, and method therefore negates the need for the user to constantly look-up on an instructional display monitor and make the complicated mappings between the displayed instructions on the monitor and the actual bone.

20 Claims, 4 Drawing Sheets

LIGHT GUIDED DIGITIZATION METHOD TO REGISTER A BONE

RELATED APPLICATIONS

This application claims priority benefit of U.S. Provisional Application Ser. No. 62/782,951 filed Dec. 20, 2018, the contents of which are hereby incorporated by reference.

TECHNICAL FIELD

The present invention generally relates to bone registration for computer-assisted orthopedic surgery, and more particularly to a system, device, and method to help guide a user in the collection of points on the bone to complete the registration.

BACKGROUND

Computer-assisted orthopedic surgery is an expanding field having applications in total joint arthroplasty (TJA), bone fracture repair, maxillofacial reconstruction, and spinal reconstruction. For example, the TSOLUTION ONE® Surgical System (THINK Surgical, Inc., Fremont, Calif.) aids in the planning and execution of total hip arthroplasty (THA) and total knee arthroplasty (TKA). The TSOLUTION ONE® Surgical System includes: a pre-operative planning software program to generate a surgical plan using an image data set of the patient's bone and computer-aided design (CAD) files of several implants; and an autonomous surgical robot that precisely mills the bone to receive an implant according to the surgical plan. In order for the computer-assisted surgical system to accurately prepare a bone, the bone needs to be registered to the surgical system. Registration determines the spatial position and orientation (POSE) of the bone relative to the coordinate system of the surgical plan and surgical system.

Several registration procedures are known in the art, illustratively including pin-based, point-to-point, point-to-surface, laser scanning, image-free, and image registration, as described in U.S. Pat. Nos. 5,951,475, 6,033,415, 8,287,522, and 8,010,177. However, the tasks required to perform these registration procedures are tedious and time consuming. The most commonly used registration procedure relies on the manual collection of several points (i.e., point-to-point, point-to-surface) on the bone using a tracked digitizer probe. A display monitor may display the points on a model of the bone to help guide the user in the point collection process. For example, the user looks at the display monitor to identify where each point needs to be collected, then re-directs their attention to the actual bone to collect those corresponding points. The user's eyes and attention are therefore constantly moving between the monitor and the bone during registration, which can make the registration process time consuming, tedious, prone to eye strain, and requires a high-level of hand-eye coordination.

In addition, the user has to accurately identify the specific location of each point on the bone as displayed on the bone model. This may be particularly difficult as the bone is minimally exposed and usually covered by biological fluids and/or tissues. This can lead to the miscollection of one or more points, which may affect registration accuracy.

Thus, there exists a need in the art for a system, device, and method to improve the point collection process during bone registration for computer-assisted surgical procedures.

SUMMARY

A projection device is provided that projects one or more points on a patient's bone to refine registration of the patient's bone. The device includes a light emitter that projects the one or more points on the patient's bone, and a tracking element. The projection device is adapted to be handheld.

A method is provided for point collection during registration of a patient's bone using the disclosed device. The method includes obtaining a set of pre-operative bone data of the patient's bone, digitizing a first set of points on the patient's bone with a digitizer probe to yield a digitized first set of points, and providing a first registration of the patient's bone and the set of pre-operative bone data using the digitized first set of points. Subsequently, a second set of points are projected directly onto the patient's bone with the disclosed device at locations needed to refine the first registration, and the second set of points are digitized on the patient's bone with the digitizer probe by following the projection of the second set of points to refine the registration of the patient's bone.

A robotic surgical system for using the disclosed device includes a surgical robot, a computing system, and a tracking system. The surgical robot includes a movable base, a manipulator arm connected to the movable base, an end-effector located at a distal end of the manipulator arm, and a force sensor positioned proximal to the end-effector for sensing forces experienced on the end-effector. The tracking system is in communication with a tracking element connected to a projection device.

BRIEF DESCRIPTION OF THE DRAWINGS

The present invention is further detailed with respect to the following drawings that are intended to show certain aspects of the present of invention, but should not be construed as a limit on the practice of the invention, wherein.

DETAILED DESCRIPTION

Figure 1:
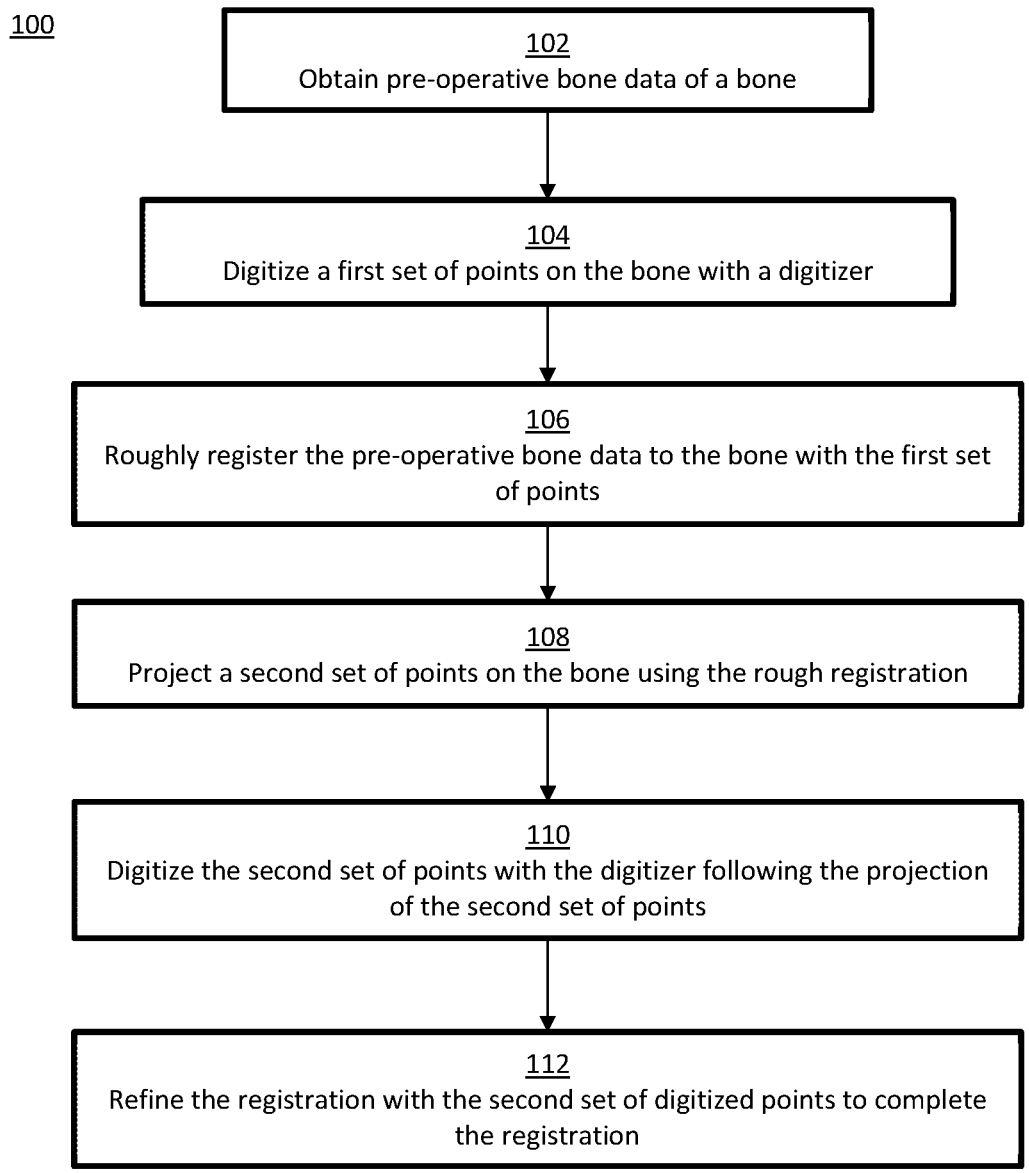
FIG. 1 depicts a method to improve the point collection process during bone registration in accordance with embodiments of the invention.

The present invention has utility as a system, device, and method to improve the point collection process during registration for computer-assisted surgical procedures. The present invention is particularly useful for guiding the user in the point collection process by projecting the points directly on the bone with a tracked digitizer probe following a rough registration of the bone. The system, device, and method therefore negate the need for the user to constantly look-up on an instructional display monitor and make the complicated mappings between the displayed instructions on the monitor and the actual bone.

The present invention is described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

Further, it should be appreciated that although the systems and methods described herein make reference to the knee, the systems and methods may be applied to other bones and joints in the body illustratively including the hip, ankle, elbow, wrist, skull, and spine, as well as revision of initial repair or replacement of any of the aforementioned bones or joints.

It is to be understood that in instances where a range of values are provided that the range is intended to encompass not only the end point values of the range but also intermediate values of the range as explicitly being included within the range and varying by the last significant figure of the range. By way of example, a recited range of from 1 to 4 is intended to include 1-2, 1-3, 2-4, 3-4, and 1-4.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

As used herein, the term "digitizer" refers to a measuring device capable of measuring physical coordinates in three-dimensional space. For example, the 'digitizer' may be: a "mechanical digitizer" having passive links and joints, such as the high-resolution electro-mechanical sensor arm described in U.S. Pat. No. 6,033,415; a non-mechanically tracked digitizer probe (e.g., optically tracked, electromagnetically tracked, acoustically tracked, and equivalents thereof) as described for example in U.S. Pat. No. 7,043,961; or an end-effector of a robotic device.

As used herein, the term "digitizing" refers to the collecting, measuring, and/or recording of physical points in space with a digitizer.

As used herein, the term "pre-operative bone data" refers to bone data used to pre-operatively plan a procedure before making modifications to the actual bone. The pre-operative bone data may include one or more of the following. An image data set of a bone (e.g., computed tomography, magnetic resonance imaging, ultrasound, x-ray, laser scan), a virtual generic bone model, a physical bone model, a virtual patient-specific bone model generated from an image data set of a bone, or a set of data collected directly on a bone intra-operatively commonly used with imageless computer-assist devices.

As used herein, the term "registration" refers to the determination of the POSE and/or coordinate transformation between two or more objects or coordinate systems such as a computer-assist device, a bone, pre-operative bone data, surgical planning data (i.e., an implant model, cut-file, virtual boundaries, virtual planes, cutting parameters associated with or defined relative to the pre-operative bone data), and any external landmarks (e.g., a fiducial marker array) associated with the bone, if such landmarks exist. Methods of registration known in the art are described in U.S. Pat. Nos. 6,033,415, 8,010,177, and 8,287,522.

Also described herein are 'computer-assisted surgical systems'. A computer assisted surgical system refers to any system requiring a computer to aid in a surgical procedure. Examples of computer-assisted surgical systems include tracking systems, tracked passive instruments, active or semi-active hand-held surgical devices and systems, autonomous serial-chain manipulator systems, haptic serial chain manipulator systems, parallel robotic systems, or master-slave robotic systems, as described in U.S. Pat. Nos. 5,086,401, 7,206,626, 8,876,830, 8,961,536, 9,707,043, and PCT Publication No/ WO/2016/049180. In particular embodiments, the surgical system is a robotic surgical system as described below.

With reference now to the drawings, FIG. 1 depicts an embodiment of a method 100 to improve the point collection process during bone registration. Pre-operative bone data of a bone is obtained (Block 102). A first set of points are digitized on the bone with a tracked digitizer probe (Block 104). The bone and pre-operative bone data are roughly registered using the first set of digitized points (Block 106). With the rough registration, a second set of points are projected directly onto the bone at locations needed to refine the registration (Block 108). The second set of points are digitized with the tracked digitizer probe by following the projection of the second set of points (Block 110). The registration is refined using the second set of digitized points to complete the registration (Block 112). Specific details and embodiments of the aforementioned are described below.

Pre-operative bone data of the bone may be collected from several sources as described above. In specific embodiments, the pre-operative bone data is a virtual model of the bone generated from an image data set of the bone. The image data set may be generated with computed tomography (CT), magnetic resonance imaging (MRI), ultrasound, X-rays, or a laser scan. The virtual model may be generated from the image data using techniques known in the art. The pre-operative bone data may further be used to plan a surgical procedure. For example, a user may position a model of an implant relative to a model of the bone to designate the best fit, fill, and/or alignment for the implant on the bone. The final pre-operative bone data, and any planning data associated therewith, may be saved and/or transferred to a computer-assisted surgical system in an operating room (OR).

In the OR, the bone is exposed in a conventional manner. The bone is subsequently fixed to a surgical system, and/or the bone is outfitted with a tracking element (e.g., a fiducial marker array, a mechanical arm, a magnetic field transmitter, inertial measurement unit) to permit the surgical system to track the bone in real-time. Once the bone is fixed and/or tracked, the bone is registered to the pre-operative bone data by the following. A first set of points are digitized on the bone. In one embodiment, the first set of points are displayed on a display monitor. Each point for collection is displayed on a model of the bone, where the user collects those corresponding points on the actual bone. In another embodiment, the first set of points are well-known anatomical landmarks. For example, the first set of points may include the medial epicondyle, lateral epicondyle, anterolateral trochlear ridge, most posterior points on the condyles. All of these landmarks are well known by the user and locatable without the use of visual guidance or instructions on a display monitor. With the first set of points, the pre-operative bone data is roughly registered to the bone. As used herein, rough registration refers to a rough match between the pre-operative bone data and the bone as measurable by at least one of the following. In one embodiment, the rough registration is calculated using significantly fewer points than the points required to refine the registration. For rough registration, approximately 3 to 10 points are collected to calculate the rough registration, whereas approximately 20 to 100 points are collected for the refined registration. In another embodiment, the rough registration is calculated using a different algorithm than the refined registration. The rough registration may be calculated using a Kabsch algorithm, or equivalent thereof. The rough registration finds the transformation between the first set of digitized points to a corresponding set of corresponding on the pre-operative bone data (e.g., P1→P1', P2→P2', where P1 is a first digitized point, and P1' is the corresponding point on a model of the bone). The refined registration may be calculated using an iterative algorithm, such as iterative closest point (ICP). The rough registration may be used as an input to the iterative algorithm. Refined registration may find the transformation from a set of points to a surface. Rather than a one to one P1→P1' determination, the iterative algorithm determines P1→ somewhere on the surface of the bone model, to refine the registration. Based on the foregoing, one should appreciate the measurable distinctions between a rough registration procedure and a refined registration procedure.

Figure 2:
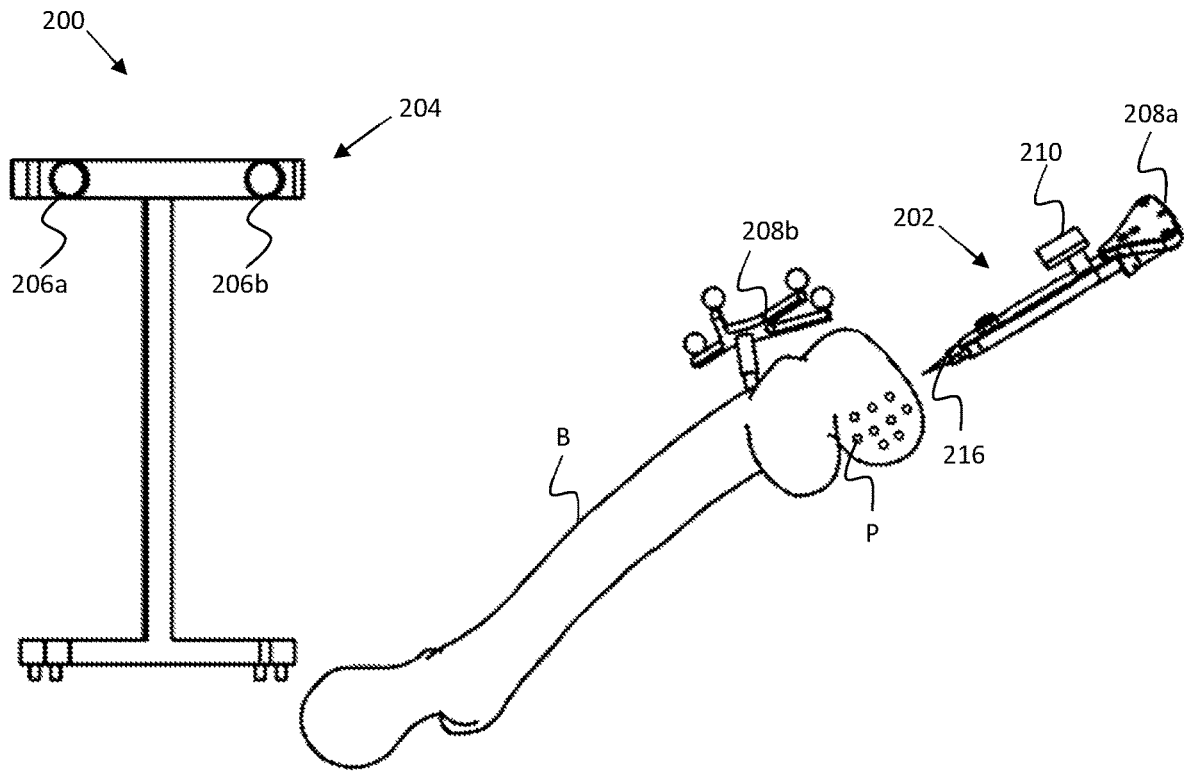
FIG. 2 depicts a system and device for projecting points on a bone in accordance with embodiments of the invention.

After the bone is roughly registered, a second set of points may be projected onto the bone to assist in the point collection process because there now exists a rough correspondence between the bone and the pre-operative bone data. With reference to FIG. 2, an embodiment of an inventive surgical system 200 is shown having a projection device 202 for projecting a set of points P on the bone B to guide a user in the point collection process to refine the registration. The system 200 may include the projection device 202 and a tracking system 204 to track the projection device 202 and the bone B in real-time. The tracking system 204 may be an optical tracking system having a pair of optical receivers (206a, 206b) (e.g., CCD cameras, CMOS cameras, or other light capturing receivers). The tracking system 204 may also be an electromagnetic, acoustic, ultrasonic, inertial measurement unit, or mechanical tracking system. The bone B and projection device 202 are outfitted with tracking elements, such as fiducial marker arrays (208a, 208b), to permit the tracking system 204 to track the bone B and the projection device 202. The projection device 202 includes a light emitter 210. The light emitter 210 projects one or more points P on the bone B based on: a) the position and orientation (POSE) of the light emitter 210; b) the POSE of the bone B; and c) the POSE of one or more points defined relative to the pre-operative bone data, which is now roughly registered to the bone B. The user can now collect points on the bone B corresponding to the location of the points P projected thereon to be used to refine registration. The user's attention is no longer diverted to a display monitor and can remain on the bone B to more efficiently and effectively collect the needed points to complete the registration.

Figure 3:
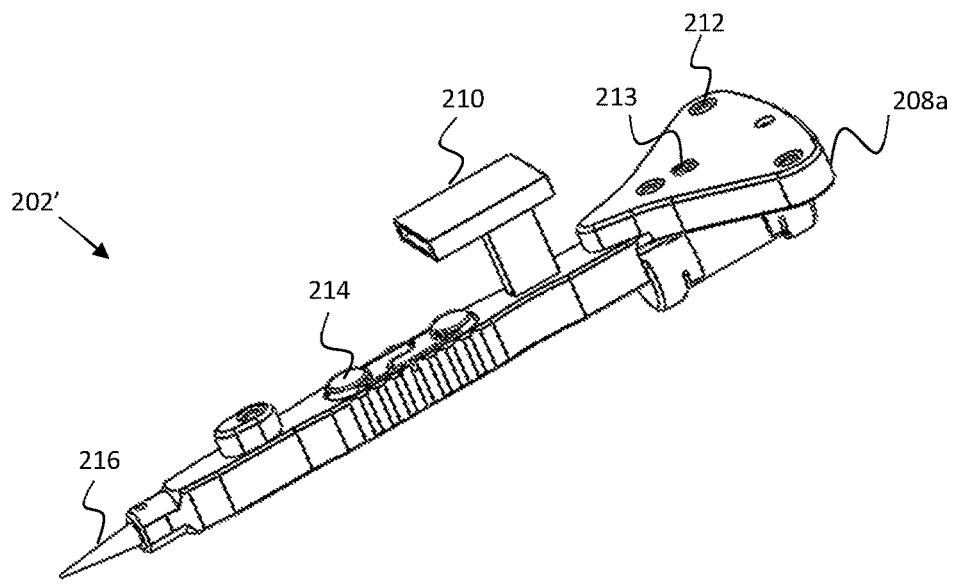
FIG. 3 depicts a projecting digitizer to project points on the bone in accordance with embodiments of the invention.

In a particular inventive embodiment, a projection device 202' is provided that functions as a projecting digitizer having the light emitter 210 connected thereto as best shown in FIG. 3. The projecting digitizer 202' may include a fiducial marker array 208a to permit the tracking of the digitizer 202' and light emitter 210. The fiducial marker array 208a may include a plurality of passive or active markers 212 viewable by the tracking system 204. The projecting digitizer 202' may further include an active emitting light emitting diode (LED) 213 for transferring data from the projecting digitizer 202' to the surgical system as described in U.S. Pat. App. Publication US2017/0245945 assigned to the assignee of the present application and incorporated by reference herein in its entirety. Data may be transferred based on the POSE of the projecting digitizer 202' or by the use of one or more input buttons 214 on the digitizer 202'. The projecting digitizer 202' also includes a probe tip 216 that contacts the bone B to designate the position of a point on the bone or other object. The light emitter 210 is attached or connected with the projecting digitizer 202'. The light emitter 210 may be a projection digitizer, pico-projector, laser, or other light-emitting device. To determine the accurate POSE of the light emitter 210 relative to the fiducial marker array 208a, the light emitter 210 may be manufactured as part of the projecting digitizer 202', where the light emitter 210 is positioned at a known location relative to the fiducial marker array 208a. Alternatively, the light emitter 210 may attachable to the projecting digitizer 202' where the relative positions between the light emitter 210 and fiducial marker array 208a is determined thereafter with techniques known in the art. This ensures the light emitter 210, and the light emitted therefrom, is known in physical space to accurately project the points P on the bone B based on: a) the POSE of the light emitter 210; b) the POSE of the bone B; and c) the POSE of one or more points defined relative to the pre-operative bone data roughly registered to the bone B. It is appreciated that the projection devices 202 and 202' are advantageously configures in the form of a stylus with the probe tip 216 distal from the fiducial marker array 208a. In certain inventive embodiments, the light emitter 210 is intermediate therebetween.

In a particular inventive embodiment, the light emitter 210 is positioned laterally offset from the axis of the projecting digitizer 202' to ensure that the points P can be projected at the probe tip 216, even when the probe tip 216 is touching the bone B. This provides some clearance between the emission of light from the emitter 210 and the digitizer 202' itself, such that the projecting digitizer 202' does not obstruct the line of light emitted from the light emitter 210.

An inventive embodiment of the point collection process with the projecting digitizer 202' may be as follows. The user wields the projecting digitizer 202' with their hand towards a projected point P. As the projecting digitizer 202' moves with the user's movements, the projected light updates in real-time such that the projected points maintain their location on the bone B. This may be accomplished by updating an image projected by the light emitter 210, or by illuminating specific LEDs or lasers inside the light emitter 210. The user then positions the probe tip 216 on a projected point P on the bone B. Once there, the user provides an input to the system, such as by pressing the input button 214 on the digitizer 202', to acknowledge that the probe tip 216 is at the designated position. Once acknowledged, the point is recorded in the system and used to refine the registration.

This point collection process continues for all of the projected points in the second set of points.

The location of the projected points may also update in real-time as each point is collected. If the refined registration occurs in real-time, the accuracy of the registration becomes more accurate with each additional point. As such, the points defined in the pre-operative data can be projected more accurately on the bone B. This is particularly advantageous to achieve a desired registration accuracy more efficiently and effectively.

Figure 4:
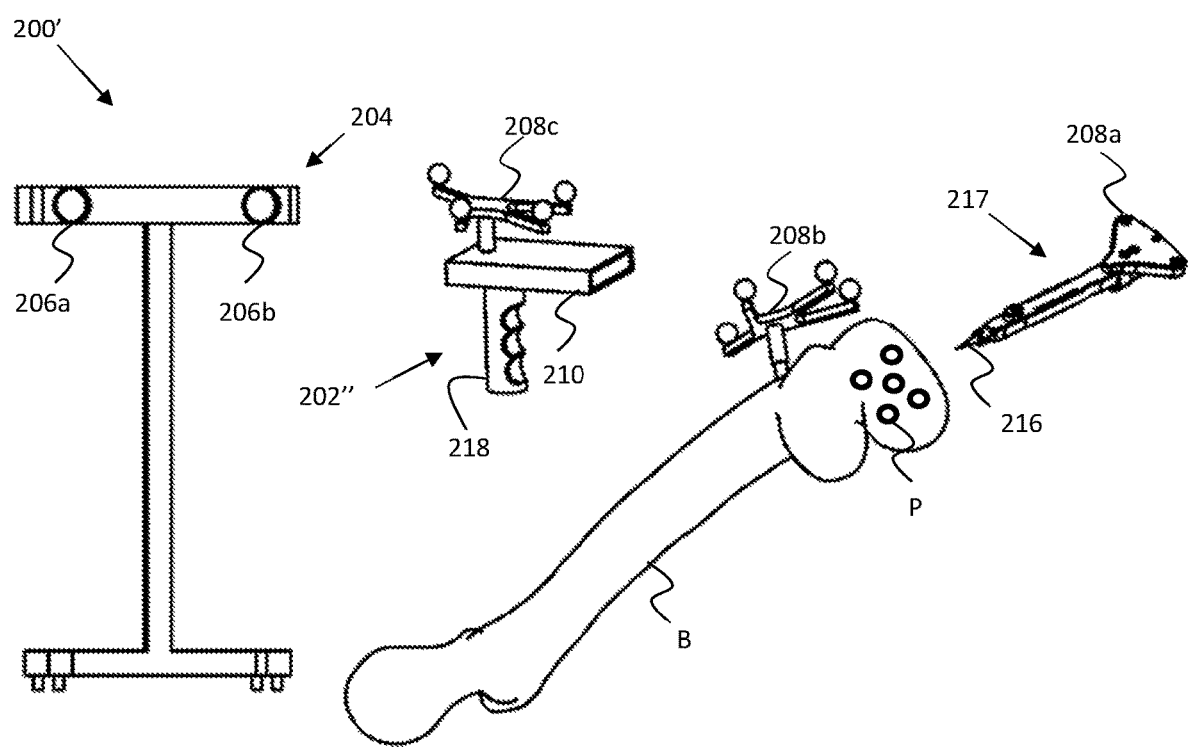
FIG. 4 depicts a system and device for projecting registration points on a bone in accordance with embodiments of the invention.

With reference to FIG. 4, an inventive embodiment of a surgical system 200' is shown having a different projection device 202". Here, the projection device 202" is a hand-held projection device 202" that is separate from a digitizer 217. The hand-held projection device 202" may include a handle 218 attached to the light emitter 210. The hand-held projection device 202" further includes a tracking element 208c to permit the tracking system 204 to track the light emitter 210 in physical space. After rough registration, a secondary user, such as an assistant in the OR, may aim the projection device 202" towards the bone B, where the light emitter 210 automatically projects one or more points on the bone B based on: a) the POSE of the tracked projection device 202"; b) the POSE of the bone B; and c) the POSE of one or more points defined relative to the pre-operative bone data roughly registered to the bone B. Because the bone B and projection device 202" are tracked, the location of the points P projected on the bone B update in real-time to maintain their location on the bone B. Another user, wielding the digitizer 217, may then collect the points P projected on the bone as described above. All, or at least a majority of the points P are collected to refine the registration of the bone with the pre-operative data and/or surgical plan.

Once the registration is complete, a computer-assisted surgical system can accurately execute a surgical procedure on the bone B.

Surgical System

Figure 5:
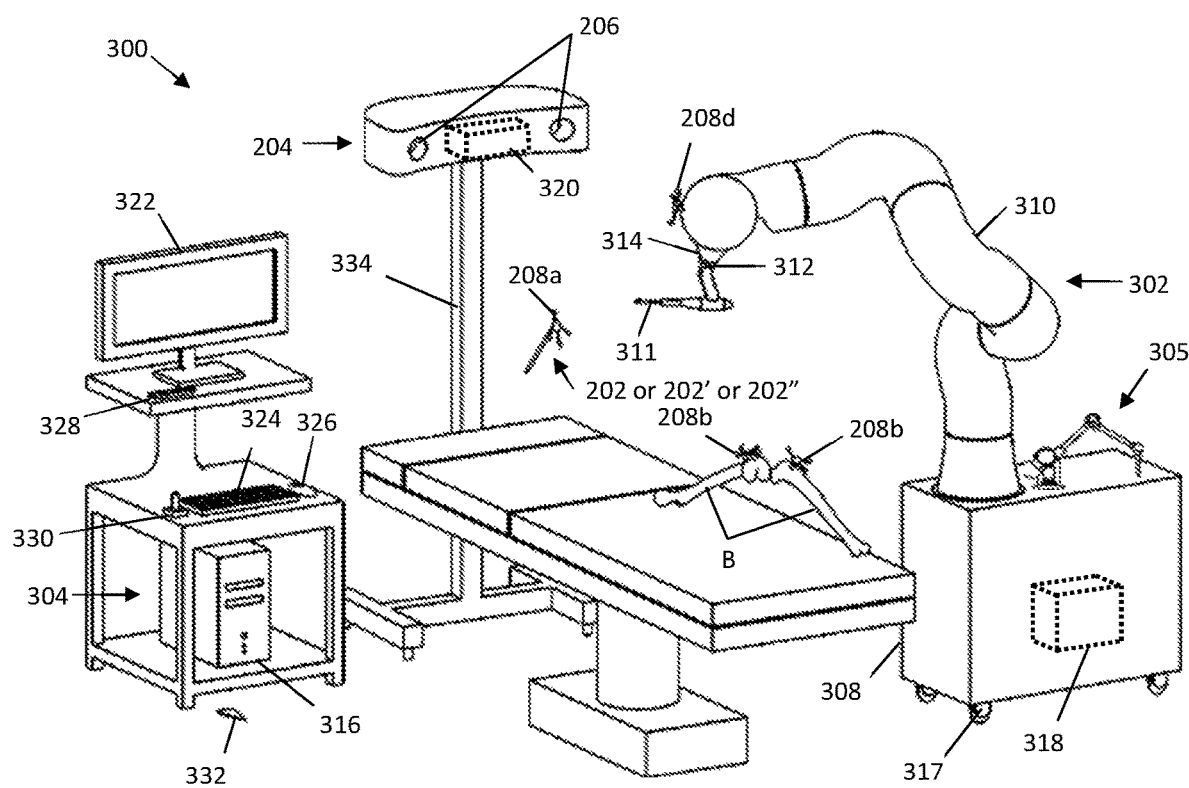
FIG. 5 depicts a robotic system in a surgical setting employing principles of the present invention in accordance with embodiments of the invention.

With reference to FIG. 5, an embodiment of a robotic surgical system 300 is shown capable of implementing embodiments of the inventive method described above. The aforementioned devices and methods are particularly useful for a robotic surgical system 300, which traditionally experience longer surgical times compared to manual techniques or techniques using hand-held tracked instrumentation.

The surgical system 300 generally includes a surgical robot 302, a computing system 304, and a tracking system 204.

The surgical robot 302 may include a movable base 308, a manipulator arm 310 connected to the base 308, an end-effector 311 located at a distal end 312 of the manipulator arm 310, and a force sensor 314 positioned proximal to the end-effector 311 for sensing forces experienced on the end-effector 311. The base 308 includes a set of wheels 317 to maneuver the base 308, which may be fixed into position using a braking mechanism such as a hydraulic brake. The base 308 may further include an actuator to adjust the height of the manipulator arm 310. The manipulator arm 310 includes various joints and links to manipulate the end-effector 311 in various degrees of freedom. The joints are illustratively prismatic, revolute, spherical, or a combination thereof.

The computing system 304 generally includes a planning computer 316; a device computer 318; a tracking computer 320; and peripheral devices. The planning computer 316, device computer 318, and tracking computer 320 may be separate entities, one-in-the-same, or combinations thereof depending on the surgical system. Further, in some embodiments, a combination of the planning computer 316, the device computer 318, and/or tracking computer 320 are connected via a wired or wireless communication. The peripheral devices allow a user to interface with the surgical system components and may include: one or more user-interfaces, such as a display or monitor 322 for the graphical user interface (GUI); and user-input mechanisms, such as a keyboard 324, mouse 326, pendant 328, joystick 330, foot pedal 332, or the monitor 322 that in some inventive embodiments has touchscreen capabilities.

The planning computer 316 contains hardware (e.g., processors, controllers, and/or memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, and generating surgical plan data. The final surgical plan may include pre-operative bone data, patient data, registration data including the POSE of the points P defined relative to the pre-operative bone data, implant position data, trajectory parameters, and/or operational data. The operational data may be a set of instructions for modifying a volume of tissue that is defined relative to the anatomy, such as a set of cutting parameters (e.g., cut paths, velocities) in a cut-file to autonomously modify the volume of bone, a set of virtual boundaries defined to haptically constrain a tool within the defined boundaries to modify the bone, a set of planes or drill holes to drill pins in the bone, a graphically navigated set of instructions for modifying the tissue, and the trajectory parameters for robotic insertion of an implant. In particular inventive embodiments, the operational data specifically includes a cut-file for execution by a surgical robot to autonomously modify the volume of bone, which is advantageous from an accuracy and usability perspective. The surgical plan data generated from the planning computer 316 may be transferred to the device computer 318 and/or tracking computer 320 through a wired or wireless connection in the operating room (OR); or transferred via a non-transient data storage medium (e.g., a compact disc (CD), a portable universal serial bus (USB) drive) if the planning computer 316 is located outside the OR.

The device computer 318 in some inventive embodiments is housed in the moveable base 308 and contains hardware, software, data and utilities that are preferably dedicated to the operation of the surgical device 302. This may include surgical device control, robotic manipulator control, the processing of kinematic and inverse kinematic data, the execution of registration algorithms, the execution of calibration routines, the execution of operational data (e.g., cut-files, the trajectory parameters), coordinate transformation processing, providing workflow instructions to a user, and utilizing position and orientation (POSE) data from the tracking system 204. In some embodiments, the surgical system 300 includes a mechanical digitizer arm 305 attached to the base 308. The digitizer arm 305 may have its own tracking computer or may be directly connected with the device computer 318. The mechanical digitizer arm 305 may act as the tracking system 204 where a digitizer probe having a light emitter 210 attached thereto is assembled to a distal end of the mechanical digitizer arm 305. In other inventive embodiments, the system includes any of the aforementioned hand-held projection devices 202 or 202' or 202", where the digitizer arm 305 acts as a stand-alone digitizer 217.

The tracking system 204 may be an optical tracking system that includes two or more optical receivers 206 to detect the position of fiducial markers (e.g., retroreflective spheres, active light emitting diodes (LEDs)) uniquely arranged on rigid bodies. The fiducial markers arranged on a rigid body are collectively referred to as a fiducial marker array (208a, 208b, 208c, 208d), where each fiducial marker array 208 has a unique arrangement of fiducial markers, or a unique transmitting wavelength/frequency if the markers are active LEDs. An example of an optical tracking system is described in U.S. Pat. No. 6,061,644. The tracking system 204 may be built into a surgical light, located on a boom, a stand 334, or built into the walls or ceilings of the OR. The tracking system computer 320 may include tracking hardware, software, data, and utilities to determine the POSE of objects (e.g., bones B, surgical device 202) in a local or global coordinate frame. The POSE of the objects is collectively referred to herein as POSE data, where this POSE data may be communicated to the device computer 318 through a wired or wireless connection. Alternatively, the device computer 318 may determine the POSE data using the position of the fiducial markers detected from the optical receivers 206 directly.

The POSE data is determined using the position data detected from the optical receivers 206 and operations/processes such as image processing, image filtering, triangulation algorithms, geometric relationship processing, registration algorithms, calibration algorithms, and coordinate transformation processing.

The POSE data is used by the computing system 304 during the procedure to update the POSE and/or coordinate transforms of the bone B, the surgical plan, and the surgical robot 302 as the manipulator arm 310 and/or bone B move during the procedure, such that the surgical robot 302 can accurately execute the surgical plan. Data from the tracking system 204 is also used to permit the projection device 202 or 202' or 202" to accurately project the points P on the bone B according to the location of the points defined relative to the pre-operative bone data as described above.

In another inventive embodiment, the surgical system 300 does not include an optical tracking system, but instead employs a mechanical arm 305 that may act as a tracking system 204 as well as a digitizer 217 or a projecting device 202'. If the bone is not tracked, a bone fixation and monitoring system may fix the bone directly to the surgical robot 302 to monitor bone movement as described in U.S. Pat. No. 5,086,401.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A method for registering a bone to pre-operative bone data, comprising:
determining a first registration between the bone and the pre-operative bone data using a first set of points digitized on the bone;
projecting light onto the bone at a plurality of pre-defined locations on the bone;
digitizing the plurality of pre-defined locations of the projected light to obtain a second set of points digitized on the bone; and
determining a second registration between the bone and the pre-operative bone data using the second set of points.

2. The method of claim 1 wherein the pre-operative bone data is a virtual model of the bone.

3. The method of claim 1 wherein the light projected at each of the plurality of pre-defined locations is a registration point and a projection device is used to project the registration point on the bone, the projection device comprising:
a light emitter configured to:
project the registration point onto a bone at a pre-defined location; and
update the projection of the registration point in response to movement of at least one of the light emitter or the bone to maintain the registration point at the pre-defined location; and
a tracking element coupled to the light emitter for a tracking system to track the movement of the light emitter.

4. The method of claim 3 wherein the projection device is adapted to be handheld.

5. The method of claim 3 wherein the light emitter is coupled to a digitizer.

6. The method of claim 5 wherein the light emitter is positioned laterally offset from an axis of the digitizer.

7. The method of claim 5 further comprising recording a location of the registration point on the bone when a tip of the digitizer contacts the bone at the pre-defined location of the projected light.

8. The method of claim 5 wherein the light emitter is positioned intermediate between a tip of the digitizer and the tracking element.

9. The method of claim 3 wherein the light emitter is configured to project a plurality of registration points on the bone at a plurality of pre-defined locations, respectively.

10. The method of claim 3 wherein the projection device further comprises a light emitting diode (LED) for transferring data between the projection device and a remote computer.

11. The method of claim 3 wherein the tracking element comprises a plurality of passive or active markers.

12. The method of claim 3 wherein the light emitter is a pico-projector or a laser.

13. The method of claim 3 wherein the tracking system is an optical tracking system.

14. The method of claim 3 wherein a plurality of pre-defined locations are pre-defined with respect to the pre-operative bone data.

15. The method of claim 14 wherein the light is projected on the bone at the plurality of pre-defined locations based on: (i) a tracked location of the projection device; (ii) a tracked location of the bone; and (iii) the first registration of the bone to the pre-operative bone data.

16. The method of claim 1 wherein the first registration is a rough registration between the bone and the pre-operative bone data.

17. The method of claim 16 wherein a number of points in the first set of points is less than a number of points in the second set of points.

18. The method of claim 16 wherein the second registration is a refinement of the first registration.

19. The method of claim 1 further comprising tracking a location of the bone with a tracking system.

20. The method of claim 1 further comprising recording a location of the registration point on the bone when a tip of a digitizer contacts the bone at the pre-defined location of the projected light.

* * * * *